(12) United States Patent
Thiebault et al.

(10) Patent No.: US 8,394,773 B2
(45) Date of Patent: *Mar. 12, 2013

(54) USE OF AN ALKYL GLYCOSIDE OR OF A MIXTURE OF ALKYL GLYCOSIDES HAVING ANTI-AGEING AND/OR CALMING PROPERTIES AS ACTIVE AGENTS IN COSMETIC COMPOSITIONS, AND METHODS OF COSMETIC CARE USING SAID COMPOSITIONS

(75) Inventors: Nicolas Thiebault, Amiens (FR); Jean-Christophe Archambault, Meung sur Loire (FR); Patrice Andre, Neuville aux Bois (FR); Florence Pilard, Amiens (FR); Vincent Moreau, Amiens (FR)

(73) Assignees: LVMH Recherche, Saint Jean de-Braye (FR); Universite de Picardie Jules Verne, Amiens (FR)

( * ) Notice: Subject to any disclaimer, the term of this patent is extended or adjusted under 35 U.S.C. 154(b) by 535 days.

This patent is subject to a terminal disclaimer.

(21) Appl. No.: 12/415,058

(22) Filed: Mar. 31, 2009

(65) Prior Publication Data

US 2009/0274760 A1 Nov. 5, 2009

(30) Foreign Application Priority Data

Apr. 2, 2008 (FR) .................................... 08 52193

(51) Int. Cl.
*A61K 31/7028* (2006.01)
*A61K 8/60* (2006.01)
*A01N 43/32* (2006.01)

(52) U.S. Cl. ......................................... 514/25; 424/401

(58) Field of Classification Search .................... 514/25; 424/401

See application file for complete search history.

(56) References Cited

U.S. PATENT DOCUMENTS

| 5,646,100 | A  | * | 7/1997 | Haugk et al. ................... 510/131 |
| 7,666,847 | B2 | * | 2/2010 | Houlmont et al. ............... 514/25 |
| 2001/0029247 | A1 | * | 10/2001 | Boures et al. ................... 514/23 |
| 2006/0046969 | A1 |  | 3/2006 | Maggio |
| 2009/0306011 | A1 |  | 12/2009 | Thiebault et al. |

FOREIGN PATENT DOCUMENTS

| WO | 2005041983 A1 | 5/2005 |
| WO | 2006107386 A1 | 10/2006 |

OTHER PUBLICATIONS

Pillai et al.; Ultraviolet radiation and skin aging: roles of reactive oxygen species, inflammation and protease activation, and strategies for prevention of inflammation-induced matrix degradation—a review; International Journal of Cosmetic Science; 2005, 27, pp. 17-34.
Seo et al.; Enhanced expression of cyloxygenase-2 by UV in aged human skin in vivo; Mechanisms of Ageing and Development.; 2003, (809): 903-910.
Takeo et al.; Synthesis of Methyl alpha- and Beta-Maltotriosides and Aryl Beta-Maltrotriosides; Carbohydrate Research, 48 (1976), pp. 197-208.
U.S. Appl. No. 12/415,136, filed Mar. 31, 2009, Amiens et al.

* cited by examiner

*Primary Examiner* — Shaojia Anna Jiang
*Assistant Examiner* — Jonathan S Lau
(74) *Attorney, Agent, or Firm* — Woodcock Washburn LLP

(57) ABSTRACT

The present invention relates to a novel use of alkyl glycosides and of mixtures of alkyl glycosides having anti-ageing and/or calming properties as active agents in cosmetic compositions, and to methods of cosmetic care using the said compositions.

33 Claims, No Drawings

USE OF AN ALKYL GLYCOSIDE OR OF A MIXTURE OF ALKYL GLYCOSIDES HAVING ANTI-AGEING AND/OR CALMING PROPERTIES AS ACTIVE AGENTS IN COSMETIC COMPOSITIONS, AND METHODS OF COSMETIC CARE USING SAID COMPOSITIONS

CROSS REFERENCE TO RELATED APPLICATION

This application claims the benefit of French Application No. 0852193, filed Apr. 2, 2008.

The present invention relates to a novel use of alkyl glycosides and of mixtures of alkyl glycosides having anti-ageing and/or calming properties, and to cosmetic compositions comprising said alkyl glycosides, and to cosmetic care methods using said compositions.

BACKGROUND

Alkyl glycosides and their applications are known in particular from the documents US 2006/0046969 and WO 2006/107386.

Patent application WO 2005/041983 discloses the use, as novel medicament advantageously intended for regulating inflammatory mechanisms, of a reducing alkylsugar monomer whose hydroxyl functional group is substituted with an alkoxy radical.

The abovementioned patent application only discloses the use, as anti-inflammatory agent, of a limited number of compounds formed of a sugar monomer.

Skin ageing is a physiological process involving environmental external factors and genetic factors. Extrinsic skin ageing results for example from chemical and physical environmental stimuli (exposure to sunlight, to UV radiation, stress, malnutrition), which damage the normal functions of the skin; intrinsic skin ageing results from a genetically programmed senescence.

The present invention relates to these two types of ageing.

A direct link has been shown between skin ageing and inflammation. Inflammation is a physiological response to any attack, for example chemical (UV, tobacco, pollution), mechanical or infectious attack, which results in the release of mediators of the prostaglandin ($PGE_2$) or cytokine (Il-8) type. These proinflammatory mediators play a direct role in skin ageing, in particular by activation of proteases (elastases) involved in the formation of wrinkles, and of enzymes (metalloproteases) which degrade the components of the dermis and epidermis, in particular the extracellular matrix (Pillai et al., Int. J. Cosmet. Sci., 2005, 27, 17-34).

Skin ageing additionally manifests itself by gradual weakening of the skin which then no longer plays its role as a barrier against external attacks as effectively. It has also been shown that the cells of the skin of elderly subjects, which have been subjected to UV radiation, express pro-inflammatory prostaglandins, in particular $PGE_2$, and cyclooxygenase-2, in a larger quantity compared to those of young subjects. The study suggests that the increased expression, in elderly subjects, of these inflammation markers could play an important role in photo-induced skin ageing (Seo et al., Mech Ageing Dev. 2003 (8-9):903-10).

Moreover, some people have a genetic predisposition which confers on them heightened skin sensitivity to environmental or chemical stimuli or to factors such as emotions, compared with the reaction observed for the same stimulus on a "normal" skin, without the skin of the predisposed persons exhibiting a pathological state as a result.

This hypersensitivity manifests itself by non-pathological inflammatory manifestations and a sensation of discomfort on the skin, and in particular by tinglings, blotches, chafing, formication or itching, sometimes accompanied by blotches. The skin type of these people is often called "sensitive skin" or "reactive skin".

It is therefore essential to have available active agents which are suitable for combating non-pathological manifestations of inflammatory origin by acting effectively on certain inflammation mediators, and which are thus capable of slowing skin ageing, of calming sensitive skins, of combating skin sensitivity and reactions of discomfort, of having a soothing, anti-irritation and antipruritus effect.

DESCRIPTION

The main aim of the present invention is to provide a novel active agent capable of combating non-pathological manifestations of inflammatory origin, such as skin ageing, whether intrinsic or extrinsic, of alleviating or suppressing the sensations of skin discomfort linked to attacks to which the skin is subjected, in particular in the case of sensitive skins.

The aim of the present invention is also to provide a novel anti-ageing and/or calming agent for sensitive skins, in particular in cosmetic compositions.

The aim of the invention is finally also to solve the technical problem by a solution which is simple, inexpensive and can be used on an industrial and cosmetic scale.

A first subject of the present invention relates to the novel use of at least one alkyl glycoside or of a mixture of at least two alkyl glycosides, as calming agent for sensitive skins and/or as agent intended to prevent or delay the appearance of the signs of intrinsic and/or extrinsic ageing of the skin, or to slow the effects thereof, in cosmetic compositions, characterized in that the alkyl glycoside, or the alkyl glycosides of said mixture, have the general formula:

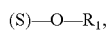

$$(S)-O-R_1,$$

(S) being an oligosaccharide formed of a sequence of 2 to 8 identical or different sugar units, and $R_1$ being an alkyl group comprising from 1 to 24 carbon atoms.

Accordingly, the present invention makes it possible to demonstrate that alkyl glycosides formed of an oligosaccharide containing at least two sugar units may be used as anti-ageing agent and/or as calming agent for sensitive skins, which makes them applicable in cosmetic compositions, in order to provide a calming effect on inflamed regions of the skin of the body or of the face under the influence of endogenous or exogenous factors, or else slow the effects of ageing on these parts of the body.

According to another aspect, the invention demonstrates, quite unexpectedly, that mixtures of alkyl glycosides in which the alkyl chains have a different length and/or which are formed from oligosaccharides having longer or shorter sequences made of sugar units, provide an effect of synergy of the cosmetic effect when the effect of mixtures of these compounds is compared to the results obtained for each of the said compounds tested individually.

This synergy effect thus allows the preparation of cosmetic compositions comprising these mixtures of alkyl glycosides as active agent, exhibiting a better efficacy at a constant dose, than for the same compositions comprising a single alkyl glycoside.

This synergy effect may also make it possible to reduce the total effective doses of alkyl glycosides, while obtaining the same cosmetic effect.

According to the invention, the oligosaccharide (S) may be formed of a sequence of 2 sugar units (disaccharide) or of 3 sugar units (trisaccharide).

According to a preferred embodiment, the sugar unit(s) is (are) pentose or hexose type reducing sugars, or a derivative of these sugars, preferably a uronic derivative, a sulphate derivative or a deoxy derivative.

According to another preferred embodiment, the sugar unit(s) is (are) chosen from arabinose, xylose, ribose, glucose, galactose, mannose, rhamnose, fucose.

According to the invention, the sugar unit(s) may be chosen equally well from the laevorotatory sugar series (L-series) or dextrorotatory sugar series (D-series), but are chosen more particularly from the dextrorotatory sugar series (D-series).

According to another particularly preferred embodiment, the sugar unit is D-glucose.

The sequence of sugar units forming the oligosaccharide may be formed of the repeat of the same sugar unit or may be formed of different sugar units.

The sequence of sugar units forming the oligosaccharide may be linear or branched.

The linkages between the sugar units are formed by a covalent glycosidic bond between the reducing group (hydroxyl) of the alcohol functional group of the hemiacetal carbon of a sugar (anomeric carbon, number 1) and the acid group (free hydrogen) of another molecule.

This bond may equally well be of the alpha or beta type, and preferably of the beta type.

The glycosidic bond may be of the 1-3 type, that is to say between the anomeric carbon No. 1 of the first sugar, and the hydroxyl group of the carbon No. 3 of the second sugar, of the 1-4 type, or of the 1-6 type.

The bond is preferably of the 1-4 type.

The conditions for the synthesis of the alkyl glycosides according to the invention make it possible to specifically obtain compounds in which the bond between the oligosaccharide (S) and the group R1 is either of the alpha type, or of the beta type, or to arrive at a mixture of the same compound of which a fraction has this alpha-type bond and the resulting fraction, the same beta-type bond.

According to the invention, the bond between the oligosaccharide (S) and the group R1 may be equally well of the alpha or beta type, preferably of the beta type.

According to the invention, the group $R_1$ is a saturated alkyl group, preferably a saturated linear alkyl group.

Preferably, the group $R_1$ is an alkyl group comprising from 1 to 18 carbon atoms, preferably a methyl or dodecyl group.

According to the invention, the oligosaccharide (S) may be chosen from maltose, cellobiose, lactose, and maltotriose.

The oligosaccharide may be laevorotatory (L-) or dextrorotatory (D-), and is preferably chosen from oligosaccharides of the (D-) series.

In particular, the oligosaccharide may be preferably chosen from beta-D-maltose or beta-D-maltotriose.

According to the invention, at least one of the alkyl glycosides may be chosen from methyl beta-D-maltoside, methyl beta-D-maltotrioside, dodecyl beta-D-maltoside, dodecyl beta-D-maltotrioside.

In a first preferred variant embodiment, the use specifically relates to a mixture composed, in particular of two alkyl glycosides such that it comprises:

an alkyl glycoside of general formula (S)—O—$R_2$, (S) being as defined above and $R_2$ being an alkyl group comprising from 1 to 6 carbon atoms; and an alkyl glycoside of general formula (S)—O—$R_3$, (S) being as defined above, and $R_3$ being an alkyl group comprising from 8 to 24 carbon atoms;

it being possible for the groups (S) of the compounds forming the mixture to be different.

In this variant embodiment, use is preferably made of a mixture composed of two alkyl glycosides which are present in a ratio of between 1/99 and 99/1, preferably of between 75/25 and 25/75, preferably still equal to about 1.

According to this variant, the group $R_2$ is a saturated alkyl group, preferably a saturated linear alkyl group, and in a particularly preferred manner a methyl group.

According to this variant, the group $R_3$ is a saturated alkyl group, preferably a saturated linear alkyl group, and in a particularly preferred manner a dodecyl group.

A first preferred mixture is formed by methyl beta-D-maltoside and an alkyl glycoside formed of a sequence of 3 sugar units, preferably dodecyl beta-D-maltotrioside.

A second preferred mixture is formed by methyl beta-D-maltotrioside and an alkyl glycoside formed of a sequence of 2 sugar units, preferably dodecyl beta-D-maltoside.

In particular, a preferred mixture is formed by the combination of two alkyl glycosides characterized in that it comprises dodecyl beta-D-maltotrioside.

According to this embodiment, a particularly preferred mixture is that formed by dodecyl beta-D-maltotrioside and methyl beta-D-maltoside.

In a second preferred embodiment, the mixture of alkyl glycosides is composed of four alkyl glycosides.

Preferably, the four alkyl glycosides are present in the mixture in substantially equal proportions.

In particular, a preferred mixture is formed by methyl beta-D-maltoside, methyl beta-D-maltotrioside, dodecyl beta-D-maltoside, dodecyl beta-D-maltotrioside.

The alkyl glycosides are used in a sufficient quantity to provide a cosmetically effective effect in relation to skin ageing and/or skin hypersensitivity.

The alkyl glycoside or the mixture of at least two alkyl glycosides as defined above are in particular used as active agents, in an effective quantity in cosmetic compositions to prevent or delay the appearance of signs of intrinsic and/or extrinsic ageing of the skin or to slow the effects thereof.

The alkyl glycoside or the mixture of at least two alkyl glycosides as defined above are also used as active agent, in an effective quantity, in cosmetic compositions to soothe or calm itching or blotches of part or the whole of the face or of the body, having as origin skin hypersensitivity.

The alkyl glycoside or the mixture of at least two alkyl glycosides as defined above are used in particular as active agent, in an effective quantity in cosmetic compositions to soothe sensitive or reactive skins.

According to the invention, the active agent is present in an amount of 0.001% to 10% by weight of the cosmetic composition containing it, in particular of 0.01% to 5% by weight of said composition.

A second subject of the present invention relates to a cosmetic composition characterized in that it comprises as active agent having an anti-ageing and/or calming effect on sensitive skins, a mixture of at least two alkyl glycosides such that the alkyl glycosides of said mixture have the general formula:

$$(S)-O-R_1,$$

(S) being an oligosaccharide formed of a sequence of 2 to 8 identical or different sugar units, and $R_1$ being an alkyl group comprising from 1 to 24 carbon atoms.

In the last two subjects according to the invention, said mixture is in particular as defined in all the preceding considerations relating to the first two subjects of the invention.

In a particularly preferred manner, a mixture of two alkyl glycosides is chosen such that it comprises in particular:
- an alkyl glycoside of general formula (S)—O—$R_2$, (S) being as defined above and $R_2$ being an alkyl group comprising from 1 to 6 carbon atoms; and
- an alkyl glycoside of general formula (S)—O—$R_3$, (S) being as defined above, and $R_2$ being an alkyl group comprising from 8 to 24 carbon atoms;

it being possible for the groups (S) of the compounds forming the mixture to be different from each other.

According to the invention, the composition further preferably comprises at least one cosmetically acceptable excipient.

In particular, the cosmetically acceptable excipient may be chosen from the group comprising pigments, colorants, polymers, surfactants, rheology-promoting agents, perfumes, electrolytes, pH-adjusting agents, antioxidants, preservatives, and mixtures thereof.

According to a preferred embodiment, the composition is intended for application to all or part of the skin of the face or of the body.

In particular, said composition may be a serum, a lotion, an emulsion, preferably a rich cream, or a hydrogel, preferably a mask, or may be provided in the form of a stick.

According to the invention, the composition preferably comprises from 0.001% to 10% by weight of one of the above-mentioned mixtures, in particular from 0.01% to 5% by weight of one of the above-mentioned mixtures.

The composition according to the invention may advantageously comprise one or more other cosmetically active agents which may be chosen from substances intended to alleviate or delay the effects of skin ageing, in particular the formation of wrinkles, by an activity aimed at promoting the maintenance of the structure of the skin and/or at limiting the degradation of the extracellular matrix of the superficial layers of the dermis and of the epidermis and/or at obtaining a skin protecting, correcting or restructuring effect; the substances having a calming, soothing or relaxing activity.

It may also further include one or more cosmetically active agents among substances having a skin lightening activity; substances having a slimming activity; substances having a moisturizing activity; substances having a skin microcirculation stimulating activity in order to enhance the radiance of the complexion, in particular of the face; substances having a seboregulating activity for the care of greasy skins; substances intended to cleanse or purify the skin; substances having an anti-free radical activity.

Finally, according to the invention, the composition contains a quantity of alkyl glycosides at an effective concentration to provide microbial growth inhibiting properties, and in particular an effective preservative effect in the said composition.

It is thus possible to prepare a cosmetic composition free of any other preservative, the active agent, consisting of an alkyl glycoside or a mixture of alkyl glycosides as described above, whose activity spectrum towards various microorganisms such as bacteria, fungi or yeasts, makes it capable of bringing about the preservation of the cosmetic composition and its microbiological stability.

In a preferred embodiment, the cosmetic composition comprising such a mixture of alkyl glycosides is free of compounds of the paraben family or of its derivatives.

A third subject of the present invention relates to a method of cosmetic care aimed at preventing or delaying the appearance of the signs of intrinsic and/or extrinsic ageing of the skin, or alleviating the effects thereof, said method comprising the application, to at least part of the body or the face, of a composition as defined above.

A final subject of the present invention relates to a method of cosmetic care aimed at calming the sensations of skin discomfort which are linked to attacks to which the skin is subjected, in particular in the case of sensitive skins, the said method comprising the application, to the relevant region of the body or the face, of a cosmetic composition as defined above.

Further aims, characteristics and advantages of the invention will emerge clearly in the light of the explanatory description which follows, made with reference to various exemplary embodiments of the invention given simply by way of illustration and which cannot therefore in any way limit the scope of the invention. In the examples, all the percentages are given by weight, the temperature is in degrees Celsius, the pressure is atmospheric pressure, unless otherwise stated.

EXAMPLES

Materials and Methods for the Syntheses and Tests

1. Synthesis of the Compounds

Unless otherwise stated, the various alkyl glycosides are synthesized according to the method described by Takeo et al. (*Carbohydrate Research*, 48 (1976) 197-208).

The method of synthesis used here differs from the publication only in the glycosylation step (grafting of the alkyl chain), in which benzene is substituted by dichloromethane ($CH_2Cl_2$) and mercury acetate is replaced by an HgO/$HgBR_2$ mixture. This step is specifically described for each of the compounds exemplified below.

The choice of the compounds of the reaction, of the catalysts and of the reaction conditions in order to carry out the reaction to its completion with a sufficient yield is well known in the state of the art.

The Products Synthesized in Order to then be Tested are the Following:

DP2-1: methyl beta-D-maltoside, prepared according to Example 1.

DP2-8: octyl beta-D-maltoside

DP2-12: dodecyl beta-D-maltoside, origin ACROS ORGANICS.

DP3-1: methyl beta-D-maltotrioside, prepared according to Example 2.

DP3-12: dodecyl beta-D-maltotrioside, prepared according to Example 3.

DP7-1: methyl beta-D-maltoheptanose

To compare the anti-inflammatory activity of the compounds of the invention with other known compounds, alkyl glycosides having a known anti-inflammatory action and described in patent application WO 2005/0419893 are synthesized.

These compounds are the following:

DP1-8: n-Octyl-beta-D-glucopyranoside, origin ACROS ORGANICS.

DP1-12: n-dodecyl-beta-D-glucopyranoside, origin ACROS ORGANICS.

2. Quantification of the Release of the Prostaglandin PGE2 and of the Interleukin Il-8

Ii has been demonstrated that keratinocytes express and release Il-8, under stimulation with interleukin-1 beta.

PGE$_2$ is an important marker of inflammatory response linked to tissue damage. It is produced by a wide variety of cells including monocytes, macrophages or keratinocytes.

Various agents can modulate the release of PGE$_2$ by the keratinocytes of the skin, such as indomethacin or plant extracts.

a) Principle of the Test

The release of the Il-8 and PGE$_2$ markers into cell line culture supernatants of immortalized keratinocytes (HaCaT), stimulated for 24 hours in the presence of oligosaccharides is quantified.

HaCaTs are cultured to 80% confluence.

A treatment is carried out over 24 hours with the product to be evaluated with, in the case of Il-8 alone, a parallel stimulation with interleukin-1.

A positive control is used by treating a column with an agent which specifically inhibits the release of each of the markers.

The culture supernatants containing the markers are collected and stored at −20° C. up to the day of the assay.

The assay is carried out with the aid of a kit specific for each of the markers.

b) Kits and Reagents Used

Kits

The assay of human Il-8 by means of the ELISA AbC204/3 kit (Abcys).

Assay of PGE2 by means of the Parameter PGE2 kit (R&D system).

Reagents

Interleukin-1β: Recombinant Human IL-1 beta, R&D Systems.

Cholecalciferol (vitamin D$_3$): Sigma

Indomethacin: Sigma c) Preparation and Treatment of the Cells

These HaCaTs are inoculated at the rate of 10 000 cells/well (supplemented KSFM culture medium, Gibco) in a 96-well microplate.

The plate is placed in an incubator (37° C. and 5% CO$_2$) for 24 hours.

The oligosaccharides, initially in the form of a 1 mM stock solution in DMSO, are exposed to the cells after suitable dilution in culture medium.

In parallel, for Il-8, the cells are stimulated with Il-1 beta at 25 ng/ml.

A column is treated with cholecalciferol (vitamin D$_3$) at 0.39 μg/ml and stimulated with Il-1 beta, as positive control inhibiting the release of Il-8.

A control column is not treated and stimulated with Il-1 beta.

A column is treated with indomethacin as positive control inhibiting the release of PGE2.

Each concentration of product, the positive control and the control without treatment, are evaluated on 4 or 6 wells of HaCaT.

d) Assay of the Markers

After 24 hours of treatment, the culture supernatants are collected and stored at −20° C.

The assay is carried out according to the protocol described in each of the kits, by an immunoenzymatic test which makes it possible to assay, by spectrophotometric measurement at 450 nm, the respective quantities of Il-8 and of PGE$_2$ present in the supernatants.

The absorbance (OD) values obtained for the 2-fold dilution series for IL-8 standard and PGE$_2$ standard (7 concentrations, in duplicate) are plotted on a logarithmic graph.

The known concentrations of IL-8 and PGE2, expressed in pg/ml, are plotted on the x-axis and the absorbance values on the y-axis, in order to obtain a straight line.

The absorbance values measured for each sample are in turn plotted on the graph, in order to determine the respective IL-8 and PGE$_2$ concentrations, expressed in pg/ml.

3. Assay of the Total Proteins

A protein assay is carried out on each well of the culture microplate.

a) Principle of the Test

The assay (in mg/ml) of the total proteins present in the cellular pellets, after treatment or non-treatment of the HaCaTs, makes it possible to relate the assay of IL-8 and of PGE$_2$ to the quantity of proteins in each well of cells, expressed in picograms (pg) of markers per milligram (mg) of proteins.

b) Kits and Reagents Used

Kit

A BCA or BiCinchoninic Acid test (BC Assay UP40840A Uptima, Interchim) is used, according to a calorimetric method.

Reagents

The assay is carried out starting with 2 solutions: bicinchoninic acid (reagent A) and copper sulphate (reagent B). The mixture of these reagents, respectively in the ratios 50:1, forms a green solution reduced to purple with Cu$^+$. These 2 reagents are present in the BCA Assay Kit from Uptima.

A standard protein solution (BSA 2 mg/ml in 0.05% NaN$_3$) is also provided in the kit in order to prepare a series.

c) Assay of the Proteins

After 24 hours of treatment, the culture supernatants of the 96-well plate are recovered.

The wells are rinsed with PBS (Phosphate Buffered Saline) before freezing the plate for a few hours.

The mixture of reagents A+B is then added after thawing the microplate, in an amount of 200 μl/well.

The plate is placed in an incubator (37° C., 5% CO$_2$) in the absence of light for 30 minutes. The absorbance may then be measured at 570 nm.

In parallel, a 2-fold diluted calibration series is prepared from a stock solution of BSA 2 mg/ml.

Expression of the Results

The absorbance values for the 6 wells are converted to mg of proteins per well of HaCaT by means of the straight line obtained by the calibration series (quantity of proteins known for an absorbance determined at 570 nm).

Finally, for each well and each treatment condition, a quantitative assay of the release of Il-8 and of PGE$_2$ is obtained, in pg/ml.

This assay is related to a quantity of proteins, expressed in mg/ml. The final quantitative result for Il-8 is therefore expressed in pg/mg of proteins.

The percentage inhibition of the production of IL-8 is calculated as follows:

$$\text{Inhibitory activity } (\%) = 100 - \frac{\text{results in the presence of the stimulated product} * 100}{\text{stimulated result without product}}$$

Exemplary Embodiments

Example 1

Synthesis of Methyl Maltoside

A solution of 5 grams of D-maltose in 220 ml of pyridine is prepared, and 80 ml of acetic anhydride (80 ml) are added.

The intermediate step specific to the method consists in adding 5.5 ml of methanol to a solution of 2,2',3,3',4',6,6'-hepta-O-acetyl-alpha-D-maltosyl bromide (2.05 g) in dichloromethane (16.5 ml), and 5.5 ml of methanol, $CaSO_4$ ground into a fine powder (2 g), HgO yellow powder (1 g) and $HgBr_2$ (49 mg) are added.

The method of synthesis leads to methyl beta-D-maltoside.

The overall yield of synthesis is 75.4%.

Example 2

Synthesis of Methyl Maltotrioside

A solution of 5 grams of D-maltotriose in 150 ml of pyridine (150 ml) is prepared, and 50 ml of acetic anhydride are added.

The intermediate step specific to the method consists in adding 6 ml of methanol to 2,2',2'',3,3',3'',4',4'',6,6',6''-deca-O-acetyl-alpha-D-maltotriosyl bromide (2.878 g) obtained at the end of the first steps of the method, in solution in dichloromethane (20 ml), and $CaSO_4$ ground into a fine powder (2 g), HgO yellow powder (1 g) and $HgBr_2$ (49 mg).

The method of synthesis according to Takeo et al. is carried out to its completion and finally leads to methyl beta-D-maltotrioside.

The overall yield of the method of synthesis is 85%.

Example 3

Synthesis of Dodecyl Maltotrioside

A solution of 1.5 grams of D-maltotriose (2.97 mmol) in 50 ml of pyridine is prepared, to which 15 ml of acetic anhydride are added.

The step specific to the method of synthesis consists in adding 6.75 ml of dodecanol to 2,2',2'',3,3',3'',4',4'',6,6',6''-deca-O-acetyl-alpha-D-maltotriosyl bromide (2.93 g) obtained at the end of the initial steps of the method, in solution in 20 ml of dichloromethane, and $CaSO_4$ ground into a fine powder (2.02 g), HgO yellow powder (1.017 g) and $HgBr_2$ (50.6 mg).

The method of synthesis according to Takeo et al. is carried out to its completion and finally leads to dodecyl beta-D-maltotrioside.

The overall yield of synthesis is 77.1%.

Example 4

Anti-Inflammatory Activity of the Alkyl Glycosides Tested Alone a) Quantification of the Release of Il-8

The test is carried out at a concentration of alkyl glycosides equal to 1 µM, after dilution in the culture medium, the negative control is pure DMSO.

The results obtained are given in Table 1 below:

TABLE 1

Anti-inflammatory activity of the alkyl glycosides of the invention

| | Control (−) | Prior art | | Invention | | | | | |
| --- | --- | --- | --- | --- | --- | --- | --- | --- | --- |
| | | DP1-8 | DP1-12 | DP2-1 | DP2-8 | DP2-12 | DP3-1 | DP3-12 | DP7-8 |
| pg IL8/mg prot | 1233.2 | 1121.6 | 930.3 | 497.7 | 377.7 | 211.0 | 346.6 | 521.5 | 711.0 |
| Standard deviation | 94.4 | 37.2 | 5.7 | 56.2 | 86.2 | 22.9 | 90.1 | 70.0 | 23.3 |
| Liberation Il-8 (%) | 100 | 91.0 | 75.4 | 40.4 | 30.6 | 17.1 | 28.1 | 79.9 | 108.9 |
| Inhibitory activity (%) | 0 | 9.1 | 24.6 | 59.6 | 69.4 | 82.9 | 71.9 | 20.1 | −8.9 | b) Quantification of the Release of $PGE_2$

The test is carried out at a concentration of alkyl glycosides equal to 1 µM, after dilution in the culture medium.

The results obtained are given in Table 2 below:

TABLE 2

Anti-inflammatory activity of the alkyl glycosides of the invention

| | Control (−) | Prior art | | Invention | | | | | |
| --- | --- | --- | --- | --- | --- | --- | --- | --- | --- |
| | | DP1-8 | DP1-12 | DP2-1 | DP2-8 | DP2-12 | DP3-1 | DP3-12 | DP7-8 |
| pg $PGE_2$/mg prot | 313.7 | 312.8 | 150.0 | 131.3 | 195.5 | 159.8 | 159.6 | 171.8 | 148.1 |
| Standard deviation | 115.7 | 127.4 | 49.1 | 22.1 | 78.9 | 71.0 | 57.8 | 51.9 | 14.4 |
| Liberation $PGE_2$ (%) | 100 | 99.7 | 47.8 | 41.8 | 62.3 | 50.9 | 50.9 | 81.2 | 70.0 |
| Inhibitory activity (%) | 0 | 0.3 | 52.2 | 58.2 | 37.7 | 49.1 | 49.1 | 18.8 | 30.0 |

Conclusions

With the exception of DP3-12 and DP7-8, the compounds tested all exhibit an anti-Il-8 activity higher than the products described in the prior art, and a PGE2 inhibiting activity equivalent to or greater than those of the prior art compounds.

DP3-12 nevertheless acts on both markers, and DP7-8 exhibits an anti-inflammatory activity that is specifically directed against the $PGE_2$ marker.

Example 5

Anti-Inflammatory Activity of Mixtures Comprising a Methyl Oligosaccharide (DPx-1) and a Dodecyl Oligosaccharide (DPy-12) with x=2 or 3, y=2 or 3, and x=y or x*y a) Activity Inhibiting the Release of IL-8

The test is carried out at a total concentration of alkyl glycosides equal to 1 μM, after dilution in the culture medium.

The percentages of inhibition of the various mixtures tested are given in Table 3 below:

TABLE 3

Anti-inflammatory activity of binary mixtures of alkyl glycosides

|  | Control (−) | A | B | C | D |
|---|---|---|---|---|---|
| pg IL8/mg prot | 1040.00 | 261.10 | 141.89 | 48.27 | 33.11 |
| Standard deviation | 132.39 | 33.32 | 12.76 | 5.62 | 4.41 |
| Liberation Il-8 (%) | 100 | 25.11 | 13.64 | 4.64 | 3.18 |
| Inhibitory activity (%) | — | 74.89 | 86.36 | 95.36 | 96.82 |

A = DP2-1 + DP2-12 (1:1)
B = DP3-1 + DP3-12 (1:1)
C = DP2-1 + DP3-12 (1:1)
D = DP2-12 + DP3-1 (1:1)

To demonstrate possible synergies as to the anti-inflammatory activity of the mixtures, the relative difference between the level of Il-8 released by the cells in the presence of each mixture in relation to the same level of Il-8 released by the cells in the presence of each of the compounds forming this mixture is evaluated.

There is synergy if the Il-8 released under the action of the mixture decreases significantly in relation to the release of Il-8 measured in the presence of each compound tested alone.

The results obtained are given in Table 4 below:

TABLE 4

Comparative anti-inflammatory activity between mixtures and individual compounds

|  |  | (2) | |
|---|---|---|---|
|  |  | DP2-12 | DP3-12 |
| (1) | DP2-1 | ΔA/(1) → −45.3% | ΔC/(1) → −90.0% |
|  |  | ΔA/(2) → +9.1% | ΔC/(2) → −94.7% |
|  | DP3-1 | ΔD/(1) → −90.1% | ΔB/(1) → −57.8% |
|  |  | ΔD/(2) → −86.1% | ΔB/(2) → −84.3% |

ΔM/(1) and ΔM/(2): relative difference (in %) between the level of release of Il-8 from the mixture M (1 + 2) in relation to the measured levels of Il-8 released from compound (1) alone and from compound (2) alone, respectively. A negative value means here that the release of Il-8 is reduced in the presence of the mixture compared with either of the compounds of this mixture. A, B, C, D: cf. Table 3 b) Activity Inhibiting the Release of $PGE_2$

The test is carried out at a total concentration of alkyl glycosides equal to 1 μM, after dilution in the culture medium.

The percentages of inhibition of the various mixtures tested are given for each mixture in Table 5:

TABLE 5

Anti-inflammatory activity of binary mixtures of alkyl glycosides

|  | Control (−) | A | B | C | D |
|---|---|---|---|---|---|
| pg $PGE_2$/mg prot | 187.0 | 173.2 | 78.2 | 156.5 | 164.0 |
| Standard deviation | 85.2 | 92.4 | 49.5 | 85.8 | 73.0 |

TABLE 5-continued

Anti-inflammatory activity of binary mixtures of alkyl glycosides

|  | Control (−) | A | B | C | D |
|---|---|---|---|---|---|
| Liberation $PGE_2$ (%) | 100 | 92.6 | 41.8 | 83.7 | 87.7 |
| Inhibitory activity (%) | 0 | 7.4 | 58.2 | 16.3 | 12.3 |

A, B, C, D: cf. Table 3

Conclusions

The anti-inflammatory activity by inhibition of release of Il-8, of mixtures comprising a methyl oligosaccharide with an oligosaccharide having a long alkyl chain, is greater than that of each of the two compounds forming the mixture. These mixtures provide a synergy of effect of inhibition of the release of Il-8, resulting in an anti-inflammatory activity that is significantly higher than that of each individual compound.

These mixtures on the other hand exhibit only a moderate anti-$PGE_2$ activity with no particular synergy.

Example 6

Anti-Inflammatory Activity of Mixtures Comprising Dodecyl Maltotrioside (DP3-12) and a Dodecyl Oligosaccharide (DPz-n) with z=2 or 3, n=1 or 12 a) Activity Inhibiting the Release of Il-8

The test is carried out at a total concentration of alkyl glycosides equal to 1 μM, after dilution in the culture medium.

The percentages of inhibition are indicated in Table 6 below for each of the mixtures tested:

TABLE 6

Anti-inflammatory activity of binary mixtures of alkyl glycosides

|  | Control (−) | B | C | E |
|---|---|---|---|---|
| pg IL8/mg prot | 1040.0 | 141.9 | 48.3 | 70.1 |
| Standard deviation | 132.4 | 12.8 | 5.6 | 4.6 |
| Liberation Il-8 (%) | 100 | 13.6 | 4.6 | 6.7 |
| Inhibitory activity (%) | 0 | 86.4 | 95.4 | 93.3 |

B = DP3-1 + DP3-12 (1:1)
C = DP2-1 + DP3-12 (1:1)
E = DP2-12 + DP3-12 (1:1)

As in Example 5, the possible synergies are evaluated by comparing the activity of each mixture B, C and E in relation to the activity of each compound forming this mixture.

The results obtained are given in Table 7 below:

TABLE 7

Comparative anti-inflammatory activity between mixtures and individual compounds

|  |  | (2) = DP3-12 |
|---|---|---|
| (1) | DP2-1 | ΔC/(1) → −90% |
|  |  | ΔC/(2) → −94.7% |
|  | DP2-12 | ΔE/(1) → −72.6% |
|  |  | ΔE/(2) → −92.3% |
|  | DP3-1 | ΔB/(1) → −57.8% |
|  |  | ΔB/(2) → −84.3% |

ΔM/(1) and ΔM/(2): relative difference (in %) between the level of release of Il-8 from the mixture M (1 + 2) in relation to the measured levels of Il-8 released from compound (1) alone and from compound (2) alone, respectively. A negative value means here that the release of Il-8 is reduced in the presence of the mixture compared with either of the compounds of this mixture.

There is synergy when the release of Il-8 under the action of the mixture is significantly reduced when it is compared to the values obtained for each compound tested alone.

b) Activity Inhibiting the Release of $PGE_2$

The test is carried out at a total concentration of alkyl glycosides equal to 1 µM, after dilution in the culture medium.

The percentages of inhibition are given in Table 8 below for each mixture:

TABLE 8

Anti-inflammatory activity of binary mixtures of alkyl glycosides

|  | Control (−) | B | C | E |
|---|---|---|---|---|
| pg $PGE_2$/mg prot | 187.0 | 78.2 | 156.5 | 112.4 |
| Standard deviation | 85.2 | 49.5 | 85.8 | 43.1 |
| Liberation $PGE_2$ (%) | 100 | 41.8 | 83.7 | 60.1 |
| Inhibitory activity (%) | 0 | 58.2 | 16.3 | 39.9 |

B, C, E: cf. Table 6

Conclusions

The anti-inflammatory activity of the mixtures comprising dodecyl maltotrioside is greater than that obtained for each compound tested alone.

The presence of dodecyl maltotrioside in the mixture provides synergy of the effect of inhibition of the release of Il-8, resulting in an anti-inflammatory activity which is significantly higher than that of each compound tested individually. It should be noted that dodecyl maltotrioside itself gives a very small effect on the release of Il-8 when it is used alone (see Example 4).

These mixtures on the other hand exhibit only a moderate anti-PGE2 activity without synergy.

Example 7

Anti-Inflammatory Activity of a Mixture of 4 Alkyl Glycosides: DP2-1, DP2-12, DP3-1 and DP 3-12 (1:1:1:1)

a) Activity Inhibiting the Release of Il-8

The test is carried out at a total concentration of alkyl glycosides equal to 1 µM, after dilution in the culture medium.

Table 9 below comprises the percentages of inhibition for the mixture, compared to each compound tested individually:

TABLE 9 anti-inflammatory activity of a mixture of four alkyl glycosides

|  | Control (−) | DP2-1 | DP2-12 | DP3-1 | DP3-12 | F |
|---|---|---|---|---|---|---|
| pg IL8/mg prot | 1040.0 | 497.7 | 211.0 | 346.6 | 521.5 | 22.5 |
| Standard deviation | 132.4 | 56.2 | 22.9 | 90.1 | 70.0 | 6.1 |
| Liberation Il-8 (%) | 100 | 40.4 | 17.1 | 28.1 | 79.9 | 2.2 |
| Inhibitory activity (%) | 0 | 59.6 | 82.9 | 71.9 | 20.1 | 97.8 |

F = DP2-1 + DP3-1 + DP2-12 + DP3-12 (1:1:1:1)

As in Examples 5 and 6, the possible synergies are evaluated by comparing the activity of the mixture F in relation to the activity of each compound forming this mixture.

The results obtained are given in Table 10 below:

TABLE 10

Comparative anti-inflammatory activity between mixtures and individual compounds

|  |  |  | F |
|---|---|---|---|
| (1) | | DP2-1 | ΔF/(1) → −94.6% |
| (2) | | DP2-12 | ΔF/(2) → −87.4% |
| (3) | | DP3-1 | ΔF/(3) → −92.3% |
| (4) | | DP3-1 | ΔF/(4) → −97.3% |

ΔF/(1), ΔF/(2), ΔF/(3), ΔF/(4): relative difference (in %) between the level of release of Il-8 from the mixture F (1 + 2) in relation to the measured levels of Il-8 released from compounds (1) to (4) alone, respectively.

A negative value means here that the release of Il-8 is reduced in the presence of the mixture compared with either of the compounds of this mixture.

b) Activity Inhibiting the Release of $PGE_2$

The test is carried out at a total concentration of alkyl glycosides equal to 1 µM, after dilution in the culture medium.

Table 11 below comprises the percentages of inhibition for the mixture, compared to each compound tested individually:

TABLE 11 anti-inflammatory activity of a mixture of four alkyl glycosides

|  | Control (−) | DP2-1 | DP2-12 | DP3-1 | DP3-12 | F |
|---|---|---|---|---|---|---|
| pg PGE$_2$/mg prot | 313.7 | 131.3 | 159.8 | 159.6 | 171.8 | 114.2 |
| Standard deviation | 115.7 | 22.1 | 71.0 | 57.8 | 51.9 | 42.7 |
| Liberation PGE$_2$ (%) | 100 | 41.8 | 50.9 | 50.9 | 81.2 | 61.1 |
| Inhibitory activity (%) | 0 | 58.2 | 49.1 | 49.1 | 18.8 | 38.9 |

F: cf Table 9

Conclusions

The mixture of the four alkyl glycosides of the invention provides synergy of the effect of inhibition of the release of Il-8, resulting in an anti-inflammatory activity which is significantly higher than that of each compound taken individually. At the same concentration, the anti-PGE$_2$ anti-inflammatory activity of the mixture is significant and comparable in intensity to that of each compound forming the mixture.

The alkyl glycosides of Example 4 and the mixtures of alkyl glycosides of Examples 5 to 7, which are representative examples of the implementation of the invention, exhibit a significant inhibitory activity towards the inflammation markers Il-8 and PGE$_2$. This characteristic activity makes them advantageous for use as active agent in dermatological compositions intended for anti-inflammatory use or in anti-ageing or calming cosmetic compositions.

Example 8

Anti-Ageing Cosmetic Emulsion Containing a Mixture of Two Glycosides According to the Invention The percentages of the formula below are expressed by weight relative to the final composition:

| Surfactant | 5 |
|---|---|
| Fatty alcohol | 2 |
| Waxes | 1.5 |
| Oils | 11.5 |
| Silicone oil | 1 |
| Polymers | 0.35 |
| Base | 0.15 |
| Methyl beta-D-maltotrioside | 0.1 |
| Dodecyl beta-D-maltotrioside | 0.1 |
| Water | qs 100 |

Example 9

Anti-Ageing Serum Containing a Mixture of Four Glycosides According to the Invention The percentages of the formula below are expressed by weight relative to the final composition:

| Glycols | 16 |
|---|---|
| Polymers | 9 |
| Polymeric gel | 8 |
| Bases | 0.1 |
| Complexing agent | 0.1 |

-continued

| Emollient | 1.8 |
|---|---|
| Solubilizing agent | 0.3 |
| Perfume | 0.1 |
| Alcohol | 5 |
| Methyl beta-D-maltoside | 0.05 |
| Dodecyl beta-D-maltoside | 0.05 |
| Methyl beta-D-maltotrioside | 0.05 |
| Dodecyl beta-D-maltotrioside | 0.05 |
| Water | qs 100 |

Example 10

Calming or Soothing Lotion for Sensitive Skins Containing a Mixture of Two Glycosides According to the Invention The percentages of the formula below are expressed by weight relative to the final composition:

| Glycol | 8.5 |
|---|---|
| Moisturizer | 0.5 |
| Phosphate buffer | 6 |
| Complexing agent | 0.2 |
| Base | 0.5 |
| Alcohol | 5 |
| Solubilizing agent | 0.2 |
| Perfume | 0.05 |
| Methyl beta-D-maltoside | 0.1 |
| Dodecyl beta-D-maltotrioside | 0.1 |
| Water | qs 100 |

Example 11

Anti-Ageing or Calming Cream Gel for Sensitive Skins Containing a Mixture of Four Alkyl Glycosides According to the Invention The percentages of the formula below are expressed by weight relative to the final composition:

| Glycol | 21 |
|---|---|
| Polymers | 1.6 |
| Complexing agent | 0.1 |
| Silicones | 1.8 |
| Emollient | 1.5 |
| Alcohol | 2 |
| Polymeric gel | 0.1 |
| Bases | 0.05 |
| Moisturizers | 1.5 |
| Methyl beta-D-maltoside | 0.05 |

| | |
|---|---|
| Dodecyl beta-D-maltoside | 0.05 |
| Methyl beta-D-maltotrioside | 0.05 |
| Dodecyl beta-D-maltotrioside | 0.05 |
| Water | qs 100 |

The invention claimed is:

1. A cosmetic composition comprising, as cosmetically active agent, a mixture of at least two alkyl glycosides wherein the alkyl glycosides of said mixture have the formula:

(S)—O—R$_1$, wherein (S) is an oligosaccharide that is maltose or maltotriose, and R$_1$ is an alkyl group comprising from 1 to 24 carbon atoms; and wherein the mixture comprises one alkyl glycoside of the formula (S)—O—R$_2$, wherein R$_2$ is an alkyl group comprising from 1 to 6 carbon atoms.

2. The cosmetic composition according to claim 1, further comprising at least one cosmetically acceptable excipient.

3. The cosmetic composition according to claim 2, wherein the cosmetically acceptable excipient is selected from the group consisting of pigments, colorants, polymers, surfactants, rheology-promoting agents, perfumes, electrolytes, pH adjusting agents, antioxidants, preservatives, and mixtures thereof.

4. The cosmetic composition according to claim 1, wherein said composition is formulated as a serum, a lotion, an emulsion, a rich cream, a hydrogel, a mask, or in the form of a stick.

5. The cosmetic composition according to claim 1, comprising from 0.001% to 10% by weight of said mixture of at least two alkyl glycosides.

6. The cosmetic composition according to claim 1, comprising a quantity of alkyl glycosides at an effective concentration to provide antimicrobial properties in said composition.

7. The cosmetic composition of claim 6, wherein the effective concentration inhibits microbial growth in said composition.

8. The cosmetic composition of claim 1, wherein the mixture of at least two alkyl glycosides is present in an amount effective to slow or delay the appearance of the signs of skin ageing.

9. The cosmetic composition of claim 1, wherein the mixture comprises
an alkyl glycoside of general formula (S)—O—R$_2$, wherein R$_2$ is an alkyl group comprising from 1 to 6 carbon atoms; and
an alkyl glycoside of general formula (S)—O—R$_3$, wherein R$_3$ is an alkyl group comprising from 8 to 24 carbon atoms.

10. The cosmetic composition of claim 1, wherein the oligosaccharide is beta-D-maltose or beta-D-maltotriose.

11. The cosmetic composition of claim 1, wherein at least one of the alkyl glycosides is methyl beta-D-maltoside, methyl beta-D-maltotrioside, dodecyl beta-D-maltoside, or dodecyl beta-D-maltotrioside.

12. The cosmetic composition of claim 1, wherein the mixture is formed by methyl beta-D-maltoside and an alkyl glycoside of the formula (S)—O—R$_1$, wherein (S) is an oligosaccharide that is maltotriose.

13. The cosmetic composition of claim 1, wherein the mixture is formed by methyl beta-D-maltotrioside and an alkyl glycoside of the formula (S)—O—R$_1$, wherein (S) is an oligosaccharide that is maltose.

14. The cosmetic composition of claim 1, wherein the mixture of alkyl glycosides is composed of four alkyl glycosides.

15. The cosmetic composition of claim 14, wherein the four alkyl glycosides are present in the mixture in substantially equal proportions.

16. The cosmetic composition of claim 1, wherein the mixture is formed by methyl beta-D-maltoside, methyl beta-D-maltotrioside, dodecyl beta-D-maltoside, and dodecyl beta-D-maltotrioside.

17. A method of cosmetic care comprising:
applying to the skin of a user identified as having sensitive or ageing skin, a cosmetic composition according to claim 1,
in an amount efficient for calming sensitive skin or for slowing or delaying the appearance or the effects of the signs of ageing of the skin.

18. The method according to claim 17, wherein the group R$_1$ is an alkyl group comprising from 1 to 18 carbon atoms.

19. The method according to claim 17, wherein the group R$_2$ is a methyl group.

20. The method according to claim 17, wherein the group R$_1$ is a dodecyl group.

21. The method according to claim 17, wherein the sugar unit(s) is a dextrorotatory sugar.

22. The method according to claim 17, wherein the oligosaccharide is selected from the group consisting of beta-D-maltose or beta-D-maltotriose.

23. The method according to claim 17, wherein at least one of the alkyl glycosides is selected from the group consisting of methyl beta-D-maltoside, methyl beta-D-maltotrioside, dodecyl beta-D-maltoside, and dodecyl beta-D-maltotrioside.

24. The method according to claim 17, wherein the mixture comprises:
an alkyl glycoside of the formula (S)—O—R$_2$; and
an alkyl glycoside of the formula (S)—O—R$_3$, wherein R$_3$ is an alkyl group comprising from 8 to 24 carbon atoms.

25. The method according to claim 24, wherein the two alkyl glycosides constituting the mixture are present in a weight ratio of between 1/99 and 99/1.

26. The method according to claim 24, wherein the group R$_2$ is a methyl group.

27. The method according to claim 14, wherein the group R$_3$ is a dodecyl group.

28. The method according to claim 24, wherein the mixture is formed by methyl beta-D-maltoside and an alkyl glycoside of the formula (S)—O—R$_3$ wherein (S) is an oligosaccharide that is maltotriose.

29. The method according to claim 24, wherein the mixture is formed by methyl beta-D-maltotrioside and an alkyl glycoside of the formula (S)—O—R$_3$ wherein (S) is an oligosaccharide that is maltose.

30. The method according to claim 17, wherein the mixture of alkyl glycosides is composed of four alkyl glycosides.

31. The method according to claim 30, wherein the four alkyl glycosides are present in the mixture in substantially equal proportions.

32. The method according to claim 30, wherein the mixture is formed by methyl beta-D-maltoside, methyl beta-D-maltotrioside, dodecyl beta-D-maltoside, and dodecyl beta-D-maltotrioside.

33. The method according to claim 17, wherein the at least one alkyl glycoside or the mixture of at least two alkyl glycosides is present in an amount of 0.001% to 10% by weight of the cosmetic composition.

* * * * *